United States Patent
Kempe

(10) Patent No.: US 6,868,854 B2
(45) Date of Patent: Mar. 22, 2005

(54) METHOD AND ARTICLE FOR TREATMENT OF FIBROMYALGIA

(76) Inventor: Frieder K. Kempe, 2536 Bluebell Avenue, Coquitlam, B.C. (CA), V3E 2H5

( * ) Notice: Subject to any disclaimer, the term of this patent is extended or adjusted under 35 U.S.C. 154(b) by 0 days.

(21) Appl. No.: 10/445,007

(22) Filed: May 27, 2003

(65) Prior Publication Data

US 2004/0237968 A1 Dec. 2, 2004

(51) Int. Cl.⁷ .............................................. A61B 19/00
(52) U.S. Cl. ........................ 128/849; 128/898; 128/846; 602/75
(58) Field of Search ................................ 128/849, 850, 128/851, 852, 853, 854, 855, 856, 898, 846, 845; 602/75, 76, 77; 139/425 R

(56) References Cited

U.S. PATENT DOCUMENTS

| | | | | |
|---|---|---|---|---|
| 3,045,815 A | * | 7/1962 | Abildgaard | 128/846 |
| 4,653,473 A | | 3/1987 | Kempe | |
| 4,825,877 A | | 5/1989 | Kempe | |
| 5,424,117 A | * | 6/1995 | Heiman et al. | 128/849 |
| 5,449,004 A | * | 9/1995 | Sanchez, Jr. | 128/845 |
| 5,561,861 A | * | 10/1996 | Lopez et al. | 128/846 |
| 5,856,245 A | * | 1/1999 | Caldwell et al. | 128/849 |
| 5,869,172 A | * | 2/1999 | Caldwell | 128/849 |
| 6,040,251 A | * | 3/2000 | Caldwell | 128/849 |
| 6,146,351 A | | 11/2000 | Kempe | |

* cited by examiner

Primary Examiner—Fadi H. Dahbour
(74) Attorney, Agent, or Firm—Oyen Wiggs Green & Mutala

(57) ABSTRACT

A method of treatment of symptoms of fibromyalgia, is disclosed. The affected patient is gowned with a radiation-shielding textile for an extended period of time, either by fashioning a garment from the textile or using a sheet or cover, or fashioning a wrap. The radiation-shielding textile found to be suitable is a cloth woven of yarn consisting of a textile fiber, such as nylon, and from two to thirty-five percent by weight of electrically conductive filament, preferably stainless steel.

8 Claims, 1 Drawing Sheet

METHOD AND ARTICLE FOR TREATMENT OF FIBROMYALGIA

TECHNICAL FIELD

The present invention relates to methods of treating symptoms of fibromyalgia.

BACKGROUND

Fibromyalgia is a widespread rheumatic condition which is characterized by chronic pain in fibrous tissues such as muscles and connective tissues, fatigue, multiple tender points, abnormal sleep patterns, stiffness, headaches, irritable bowels numbness and other symptoms. It is also associated with chronic fatigue syndrome. The cause of fibromyalgia is unknown and there are no known cures. Various medications are used to treat fibromyalgia, as well as hypnosis, but there are no known medications which permanently relieve its symptoms.

The inventor of the present invention has previously discovered that pain resulting from exposed or damaged nerve ends, commonly referred to as phantom limb pain, can be relieved or alleviated by shielding the painful area with a cloth woven from a yarn containing threads of a conductive metal. As disclosed in U.S. Pat. No. 4,653,473, the contents of which are incorporated herein by reference, which issued to the inventor on 31 Mar., 1987, this pain reduction method has also been found to be effective to reduce stump spasms and stump pains in amputees, pain from scars other than those resulting from amputation and also arthritic pain and menstrual pain and cramps.

The yarn of the cloth used in this previously-discovered method is preferably composed of from 2 to 35% by weight of conductive metal filament, and the balance of natural or synthetic textile fiber such as nylon. The metal may be any conductor, but a stainless steel alloy has been found to be effective.

The inventor of the present invention has also discovered that a similar method can be used to relieve muscle pain and soreness and reduce nervousness in horses. This method of treating horse pain and nervousness comprises fashioning a horse blanket of a cloth woven from a yarn containing threads of conductive metal, and placing it on the horse. This method is disclosed in U.S. Pat. No. 4,825,877, the contents of which are incorporated herein by reference, which issued to the inventor of the present invention on 2 May, 1989. The inventor of the present invention has also discovered that a similar method can be used to alleviate delayed onset muscle soreness as disclosed in U.S. Pat. No. 6,146,351 issued 14 Nov., 2000, the contents of which are incorporated herein by reference. See also Zhang J., Clement D, and Taunton J. "The Efficacy of Farabloc, an Electromagnetic Shield, in Attenuating Delayed-Onset Muscle Soreness" Clin J. Sport Med, 2000 January; 10(1): 15–21. PMID: 106995845 [PubMed—indexed for MEDLINE].

It has now been discovered that a similar method may be implemented sucessfully in the treatment of fibromyalgia in humans.

SUMMARY OF INVENTION

The present invention provides a method of treatment of symptoms of fibromyalgia in a patient comprising gowning the patient with a radiation-shielding textile for a period of time sufficient to reduce the symptoms of fibromyalgia, wherein the radiation-shielding textile comprises between two and thirty-five percent by weight of a continuous system of electrically-conductive fibers and the remainder of non-conductive fibers.

The invention further provides a method of treatment of symptoms of fibromyalgia in a patient comprising the steps of: (i) providing an article of clothing configured to substantially cover the affected areas of the trunk of the body of the patient with a cloth comprising between two and thirty-five percent by weight of a continuous system of electrically conductive fibres; and (ii) the patient wearing the article of clothing whereby the affected areas of the trunk of the body of the patient are substantially covered by the conductive cloth over a period of time sufficient to reduce the symptoms.

The invention further provides a gown constructed of a radiation-shielding textile, wherein the radiation-shielding textile comprises between two and thirty-five percent by weight of a continuous system of electrically-conductive fibers and the remainder of non-conductive fibers. The cloth may be a woven or knitted cloth and the conductive fibers may be stainless steel fibers or other conductive material such as ceramics.

BRIEF DESCRIPTION OF DRAWINGS

In drawings which illustrate embodiments of the invention.

DESCRIPTION

Figure 1:
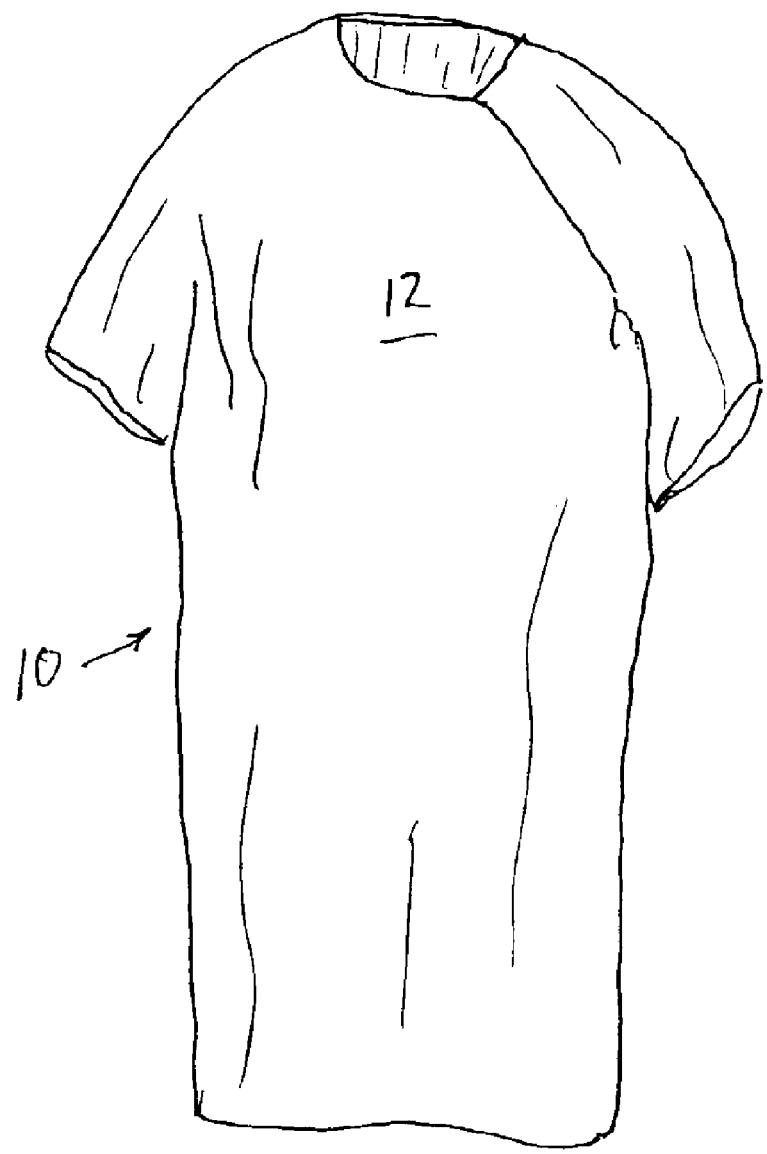
FIG. 1 illustrates a hospital gown made from a cloth according to the invention.

For purposes of this application, "gowning" means covering substantially the affected areas of the trunk of the patient. This may be accomplished, for example, by clothing in a cover, gown or other form of apparel or wrapping with a sheet of textile.

A suitable covering material for the practice of the method of the invention which both provides the appropriate electromagnetic shielding and the comfort of a standard non-metallic textile is a fabric sold under the trade-mark FARABLOC. The yarn from which the textile is woven is preferably composed of approximately 13% by weight of stainless steel filaments but may be from 2% to 35% by weight of stainless steel filaments. The balance of the yarn is a synthetic nylon fiber such as nylon. The yarn has an electrical conductance of approximately 330 ohms per centimeter. The preferred fabric has a warp of 24.5 threads per centimeter and a woof of 24.5 threads per centimeter but fabrics of other characteristics, such as knitted fabrics also will be effective. The weight of the woven fabric is preferably approximately 180 grams per square meter. The preferred binding is L 1/1—that is, one thread up and one thread down. Other conductive materials would also be suitable for the conductive fibers, such as copper, silver or ceramics. Other natural or synthetic non-conductive fibers would also be suitable to comprise the yarn. It would also be suitable to utilize cloth woven of alternate threads of conductive and textile fibers.

At the basis of the present invention is the discovery that use of FARABLOC metallic cloth also has beneficial results in the alleviation of the symptoms of fibromyalgia.

According to the method of the invention, the fibromyalgia sufferer wears, for example, a gown as designated by reference numeral 10 in FIG. 1. The longer the period during which the gown is worn, the better the results, but preferably the gown is worn at least while the patient is sleeping during the night. The gown 10 need not be constructed entirely of the conductive cloth, but the gown should have a large enough area of the conductive cloth 12 to substantially cover the affected areas of the trunk of the patient's body. While the method preferably uses a gown 10, other forms of apparel such as a shirt and pants or jumpsuit may be used, or a sheet or wrap secured about the patient's body using hook and loop fasteners, for example.

Summary of the First Study

In a first study carried out on 126 patients hospitalized for 20 days, a double blind placebo controlled study was conducted to assess the efficacy of a FARABLOC gown worn at night compared to a placebo gown in alleviating the symptoms of fibromyalgia. Exclusion criteria included recent trauma, secondary fibromyalgia and inappropriate blood parameters. Inclusion criteria focussed on the classic bilateral nine point tender positions of fibromyalgia, scaled from zero to four. All drugs were stopped but paracetamol was provided on demand. Physiotherapy was consistently provided to all patients. Of the 126 patients who took part in the study, 84 wore placebo gowns and 42 wore FARABLOC gowns. Variables of total tenderness of the 18 fibromyalgia points, overall pain using the visual analogue scale and total drug use were assessed on admission and on discharge after 20 days in hospital. The following are the results of the first study.

|  | FARABLOC | PLACEBO |
|---|---|---|
| # of subjects | 42 | 84 |
| Age (years) | 49.02 | 48.08 |
| SEX |  |  |
| Female | 35 | 72 |
| Male | 7 | 12 |
|  | MEAN +/− SD | MEAN +/− SD |
| TOTAL TENDERNESS |  |  |
| Admission | 48.86 +/− 3.71 | 49.40 +/− 4.02 |
| Discharge | 38.21 +/− 6.17 | 46.87 +/− 3.43 |
| Difference | 10.64 +/− 5.69 | 2.54 +/− 3.40 |
| TOTAL PAIN |  |  |
| Admission | 7.41 +/− 0.49 | 7.41 +/− 0.52 |
| Discharge | 5.39 +/− 0.99** | 6.83 +/− 0.59 |
| Difference | 2.03 +/− 0.99** | 0.59 +/− 0.71 |
| TOTAL DRUG USE | 10.69 +/− 6.68** | 26.12 +/− 9.37 |

**P < 0.001—Paired t-test

Conclusion:

There was a strong positive effect of Farabloc on total tenderness, total pain and drug use in the study of fibromyalgia patients during 20 days of hospitalization.

Summary of the Second Study

In a second study carried out on 25 patients hospitalized for 21 days, a double blind crossover study was conducted to assess the efficacy of a FARABLOC gown compared to a placebo gown in alleviating the symptoms of fibromyalgia. Exclusion criteria included recent trauma, secondary fibromyalgia and inappropriate blood parameters. Inclusion criteria focussed on the classic bilateral nine point tender positions of fibromyalgia, scaled from zero to four. All drugs were stopped but paracetamol was provided on demand. Physiotherapy was consistently provided to all patients. All patients were provided with new gowns on admission and at midpoint of the 21 day hospital period. This created three distinct groups who switched gowns as described. Variables of total tenderness of the 18 fibromyalgia points, overall pain using the visual analogue scale and total drug use were assessed on admission, midpoint and on discharge. The data was analyzed from the midpoint to the discharge period by assessment of change in three variables. The following are the results of the second study.

|  | GOWN ORDER FARABLOC/PLACEBO | GOWN ORDER PLACEBO/PLACEBO | GOWN ORDER PLACEBO/FARABLOC |
|---|---|---|---|
| # subjects | 11 | 7 | 7 |
| CHANGE IN TENDERNESS | −6.5 +/− 5.559** | −0.29 +/− 2.56 | 8.71 +/− 4.75** |
| CHANGE IN PAIN | −13.27 +/− 11.40** | −4.43 +/− 5.80 | 16.00 +/− 8.35** |
| CHANGE IN DRUG USE | −18.00 +/− 5.27** | −16.00 +/− 5.10 | −9.29 +/− 4.39** |

**P < 0.001—Paired t-test

Conclusion:

This study supports the hypothesis that Farabloc reduces tenderness and pain in fibromyalgia patients.

As will be apparent to those skilled in the art in the light of the foregoing disclosure, many alterations and modifications are possible in the practice of this invention without departing from the spirit or scope thereof. For example, while a woven cloth has been specified in the description of the preferred embodiment, it will be apparent to those skilled in the art that a non-woven cloth having a grid of conductive filaments will also operate effectively in the method of the invention while retaining the qualities of a normal fabric. It will also be apparent that many variations in the type of conductive thread or yarn and textile fibers used in the cloth and in the manner of weaving or knitting the cloth are possible in the practice of this invention without departing from the scope thereof. Accordingly, the scope of the invention is to be construed in accordance with the substance defined by the following claims.

What is claimed is:

1. A method of treatment of symptoms of fibromyalgia in a patient comprising gowning said patient with a radiation-shielding textile for a period of time sufficient to reduce said symptoms of fibromyalgia, wherein said radiation-shielding textile comprises between two and thirty-five percent by weight of a continuous system of electrically conductive fibers and the remainder of non-conductive fibers.

2. The method of claim 1 wherein said radiation-shielding textile is a woven cloth and said electrically conductive fibers are stainless steel fibers.

3. The method of claim 1 wherein said radiation-shielding textile is a woven cloth slid said electrically conductive fibers are formed of a material selected from the group copper, silver or ceramic.

4. The method of claim 1 wherein said radiation-shielding textile comprises about thirteen percent by weight of a continuous system of electrically conductive fibers and the remainder of non-conductive fibers.

5. A method of treatment of symptoms of fibromyalgia in a patient comprising the steps of:
   (i) providing an article of clothing configured to substantially cover the affected areas of the trunk of the body of the patient with a cloth comprising between two an thirty-five percent by weight of a continuous system of electrically conductive fibres; and
   (ii) said patient wearing said article of clothing whereby said trunk of the body of said patient is substantially covered by said cloth over a period of time sufficient to reduce said symptoms.

6. The method of claim 5 wherein said cloth is a woven cloth and said electrically conductive fibers are formed of a material selected from the group copper, silver or ceramic.

7. The method of claim 5 wherein said cloth comprises about thirteen percent by weight of a continuous system of electrically conductive fibers and the remainder of non-conductive fibers.

8. The method of claim 5 wherein said cloth is a woven cloth and said electrically conductive fibers are stainless steel fibers.

* * * * *